United States Patent [19]

Cooper

[11] Plant 4,676

[45] Mar. 24, 1981

[54] SEMI-SPUR MUTANT STRAIN OF GRANNY SMITH APPLE TREE

[75] Inventor: Calvin Cooper, Brewster, Wash.

[73] Assignee: Granspur Enterprises, Orondo, Wash.

[21] Appl. No.: 5,294

[22] Filed: Jan. 22, 1979

[51] Int. Cl.[3] ..... A01H 5/00
[52] U.S. Cl. ..... Plt./34
[58] Field of Search ..... Plt./34

[56] References Cited

U.S. PATENT DOCUMENTS

P.P. 3,453 1/1974 Hannaford ..... Plt./34

*Primary Examiner*—Robert E. Bagwill
*Assistant Examiner*—James R. Feyrer
*Attorney, Agent, or Firm*—Christensen, O'Connor, Johnson & Kindness

[57] ABSTRACT

A new and distinct variety of 'Granny Smith' apple tree characterized by its semi-spur growth characteristics, with node spacings approximately intermediate those of 'Stardard' and 'Hannaford' (U.S. Plant Pat. No. 3,453), and by its fruit having distinct dark green stripes imposed on a lightly mottled green background.

3 Drawing Figures

1

This invention or discovery relates to a new mutant strain of the standard Granny Smith apple tree. It was discovered growing in the cultivated orchard of Calvin Cooper near Brewster, Wash., and has been reproduced through successive generations, by grafting in said orchard and in the orchard of Grady Auvil near Orondo, Wash., establishing the genetic stability of the distinguishing characteristics of this new strain or sport.

In the accompanying photographs, two show the growth habit, including the fruit distribution of the new variety, and the third shows side by side comparisons of the fruit of the new variety, those having dark green stripes on a light green background, with fruit of the standard Granny Smith variety without stripes.

Parentage: Sport of standard 'Granny Smith'.

Date of fruit maturity: Matures at the same time as stardard 'Granny Smith'. In the Orondo, Wash. area: Oct. 10 on M 26 to Oct. 14 on M 7A.*

Tree: Medium size, vigorous, more spurs per linear foot of branch than parent, resulting in a more dense tree canopy, heavy production, annual bearer.

*Trunk.*—Medium thick, spurs closer together than parent strain. Internode length intermediate, percentage leaf axillary buds developing spurs higher than parent strain.

*Leaves.*—Large, ovate, point tapered, margin slightly serrate. Typical: length 3⅝ inches; width 2¼ inches; color, dark yellowish green (2.5G 4/6)[1]; petiole — long, medium thick, moderately pubescent.

Flowers:

*Date of first bloom.*—April 25.

*Date of full bloom.*—April 28.

*Color.*—Petals white to very pale purple (7.5P 9/2)[1], stigma and style light green (5GY 8/8)[1].

Fruit:

*Maturity when described.*—Mature from mid-season storage.

*Size.*—Medium to large. Equatorial diameter 3 inches to 3¾ inches.

*Form.*—Uniform, rounded to oblate.

2

*Cavity.*—Smooth, deep, conical, symmetrical. Depth ⅝ to ⅞ inches; breadth, 1¼ to 1½ inches; base of stem cavity occasionally russets.

*Stem.*—Medium to light, flexible, well attached.

*Basin.*—Smooth, calyx lobes absent (not glabrous as in 'Delicious'). Depth ½ to ⅝ inches; breadth, 1½ inches.

*Calyx.*—Sepals pointed, open, pubescent, prominent in broad basin.

*Skin.*—Smooth, glossy, medium thick. Dots — small, white, inconspicuous. Distribution relatively few on fruit shoulders, more numerous toward basin. Color: background green (5GY 8/8)[1] with irregular green stripes (7.5GY 7/9)[1]. Exposure to sunlight results in 'blush' of varying intensity with color ranging from yellow-pink to yellow-brown. Skin flavor tart.

*Flesh.*—White, juicy, crisp. Cut surfaces non-browning. Flavor mild. Quality good.

*Core.*—Core line prominent in cross-section, medium size; ovate seed cavities, vascular bundles evenly spaced and inconspicuous; calyx tube closed, narrow, inconspicuous, long; styles persistent, united.

*Stamen.*—In single whorl, persistent.

Seeds: Seed number 4 to 6 at maturity, occasionally more than 1 per cell. Length 9/32 to 5/16; breadth, 3/16 inch. Form acute, color reddish brown to chestnut (mixed 10YR 5/6, 10YR 4/4).

Use: Dessert, baking, processing.

Keeping quality: Very good; 160 days in cold storage; shelf life very good.

Unique physical characteristics of fruit: The stripe effect of the coloration is unique to this cultivar of the 'Granny Smith' variety.

Comparison: Examined under field conditions, trees of this new variety growing side by side with trees of standard 'Granny Smith' at the Auvil Fruit Orchard in Orondo, Wash., during each of two summers, 1978 and 1979, revealed distinct differences in growth habit and fruit coloration. The internode distance in the new variety is shorter than that in the parent strain. (It is also somewhat longer than that in the Hannaford spur strain, U.S. Plant Pat. No. 3,453, also growing in the same orchard and compared at the same times). The new variety may thus properly be characterized as having an intermediate spur-type growth habit. Fruit of the new variety has a distinctive green stripe of a somewhat irregular pattern on a lighter green background, a coloration effect that is unique in 'Granny Smith' cultivars.

*Where M26 and M7A are rootstock designations.

[1]Color plate number from Nickerson Color Fan, distributed by American Horticultural Council. Arnold Arboretum, Jamaica Plain 30, Massachusetts.

I claim:

1. A new and distinct variety of Granny Smith apple tree, substantially as described and illustrated, characterized by its semi-spur growth characteristics with internodal spacing generally intermediate that of the standard Granny Smith variety and the Hannaford variety (U.S. Plant Pat. No. 3,453), and by its fruit having distinct dark green stripes, the predominant color of Hannaford fruit, superimposed on a slightly mottled lighter green color, the predominant color of standard Granny Smith fruit.

* * * * *

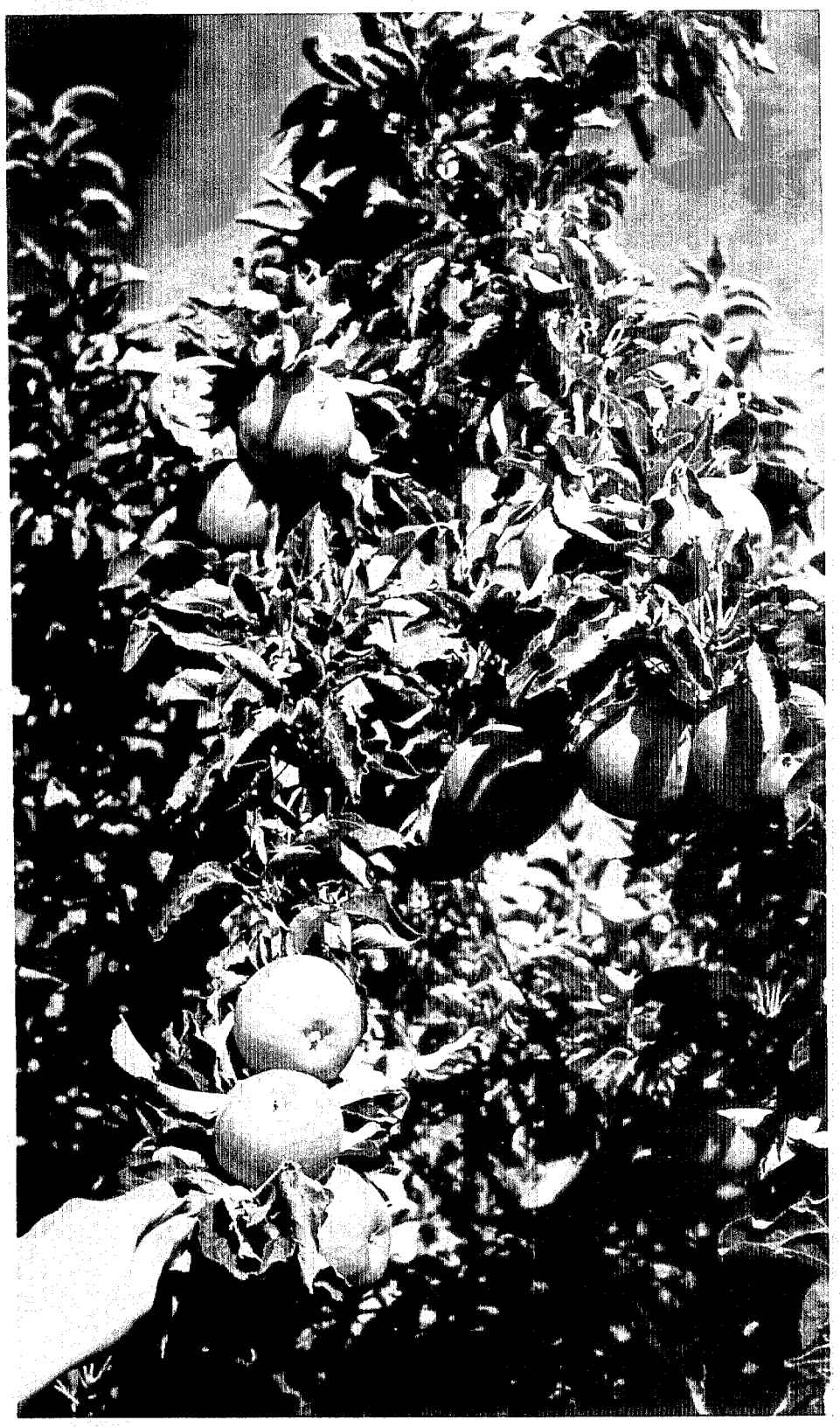

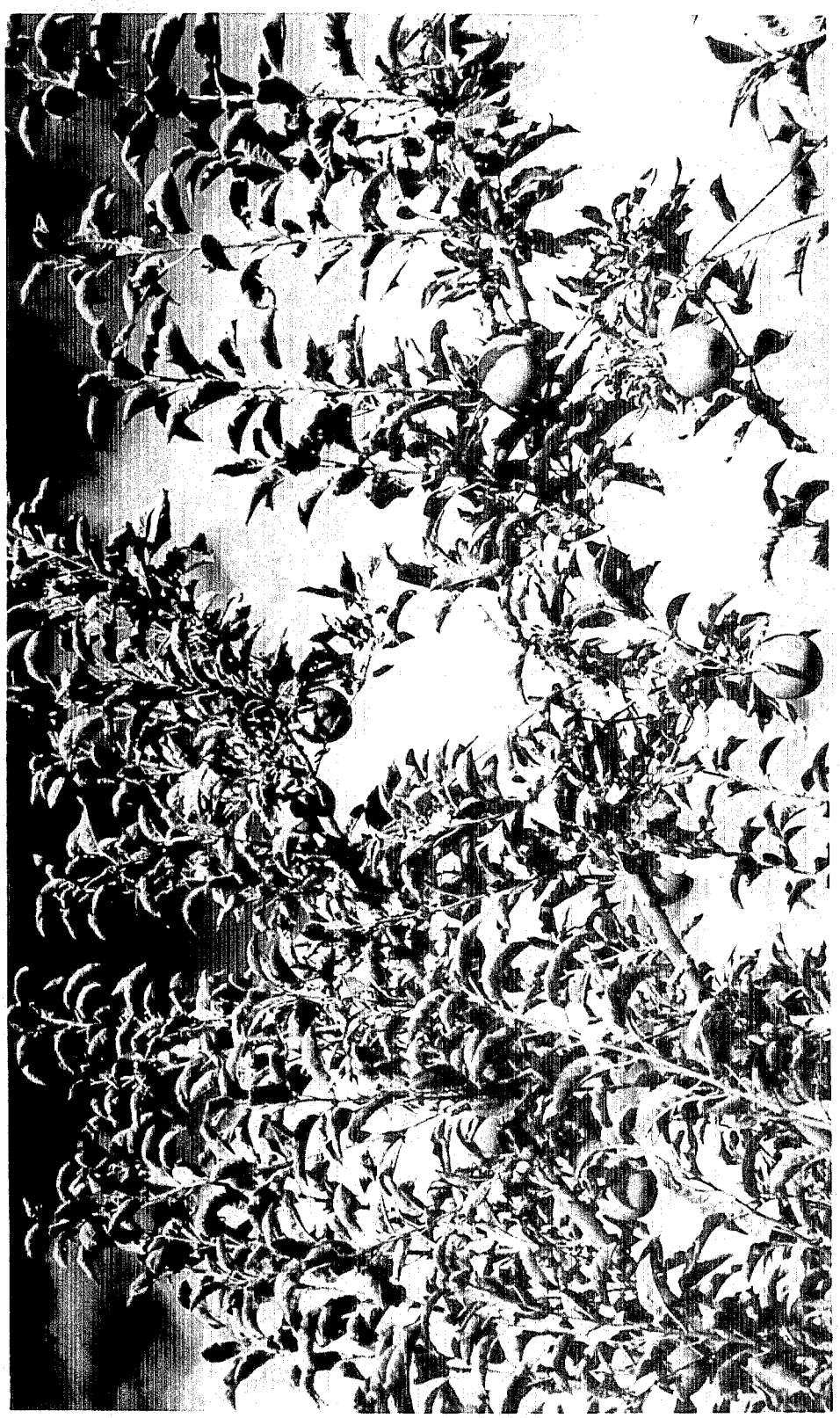

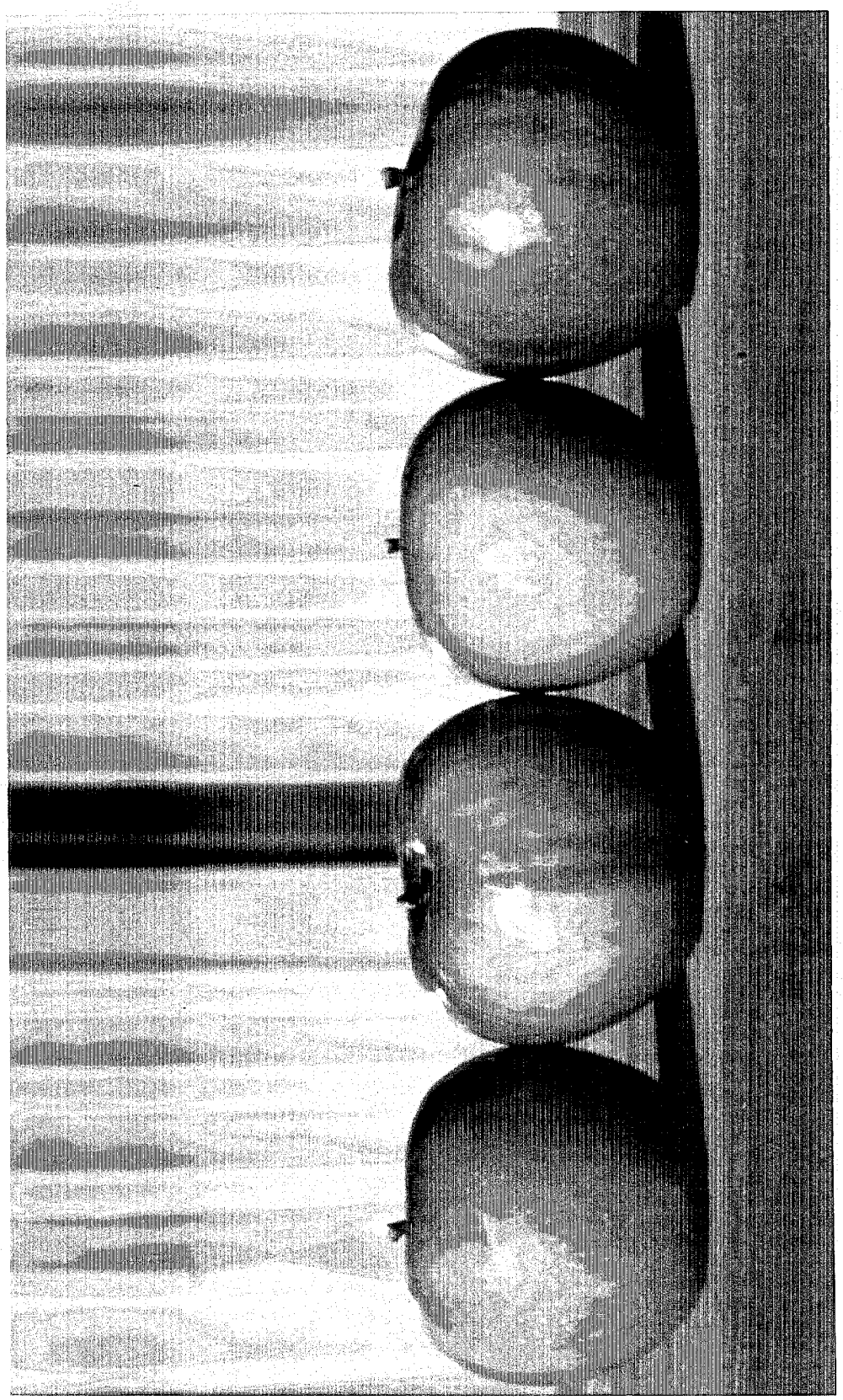

UNITED STATES PATENT AND TRADEMARK OFFICE

CERTIFICATE OF CORRECTION

PATENT NO. : PP 4,676

DATED : March 24, 1981

INVENTOR(S) : Calvin Cooper

It is certified that error appears in the above-identified patent and that said Letters Patent are hereby corrected as shown below:

Abstract: "Stardard" is changed to --Standard--.

Column 1, line 18: "stardard" is changed to --standard--.

Signed and Sealed this

*Eleventh* Day of *August 1981*

[SEAL]

*Attest:*

GERALD J. MOSSINGHOFF

*Attesting Officer* *Commissioner of Patents and Trademarks*